United States Patent
Smith et al.

(10) Patent No.: US 11,116,762 B2
(45) Date of Patent: Sep. 14, 2021

(54) COMPOUNDS, COMPOSITIONS, AND METHODS FOR TREATING HUMAN IMMUNODEFICIENCY VIRUS

(71) Applicant: OYAGEN, INC., Rochester, NY (US)

(72) Inventors: Harold C. Smith, Rochester, NY (US); Ryan P. Bennett, Clifton Springs, NY (US)

(73) Assignee: OyaGen, Inc., Rochester, NY (US)

( * ) Notice: Subject to any disclaimer, the term of this patent is extended or adjusted under 35 U.S.C. 154(b) by 0 days.

(21) Appl. No.: 16/476,094

(22) PCT Filed: Jan. 2, 2018

(86) PCT No.: PCT/US2018/012098
§ 371 (c)(1),
(2) Date: Jul. 4, 2019

(87) PCT Pub. No.: WO2018/128993
PCT Pub. Date: Jul. 12, 2018

(65) Prior Publication Data
US 2019/0350925 A1 Nov. 21, 2019

Related U.S. Application Data

(60) Provisional application No. 62/442,374, filed on Jan. 4, 2017.

(51) Int. Cl.
*A61K 31/4745* (2006.01)
*A61K 45/06* (2006.01)
*A61P 31/18* (2006.01)

(52) U.S. Cl.
CPC .......... *A61K 31/4745* (2013.01); *A61K 45/06* (2013.01); *A61P 31/18* (2018.01)

(58) Field of Classification Search
CPC .............. A61K 31/4745; A61K 31/496; A61K 31/513; A61K 31/551; A61K 31/7072; A61K 45/06; A61P 31/18
See application file for complete search history.

(56) References Cited

U.S. PATENT DOCUMENTS

| | | | |
|---|---|---|---|
| 6,689,761 B1 * | 2/2004 | Chodakewitz | A61P 31/12 514/49 |
| 10,588,902 B2 * | 3/2020 | Smith | G01N 33/6845 |
| 2002/0193391 A1 | 12/2002 | Bouscarel et al. | |
| 2003/0165846 A1 | 9/2003 | Marino et al. | |
| 2007/0212756 A1 | 9/2007 | Greene et al. | |
| 2008/0167199 A1 | 7/2008 | Zhang et al. | |
| 2010/0029570 A1 | 2/2010 | Zhang et al. | |
| 2015/0272959 A1 * | 10/2015 | Smith | A61K 31/47 514/229.5 |
| 2015/0366984 A1 | 12/2015 | Sun | |
| 2016/0143900 A1 | 5/2016 | Smith | |

FOREIGN PATENT DOCUMENTS

| | | |
|---|---|---|
| WO | 1991/016904 A1 | 11/1991 |
| WO | 2014/055944 A1 | 4/2014 |
| WO | 2014/186423 A1 | 11/2014 |
| WO | 2014/210082 A2 | 12/2014 |

OTHER PUBLICATIONS

Nathans et al., "Small-molecule inhibition of HIV-1 Vif", 2008, Nature Biotechnology, 26(10), pp. 1187-1192. (Year: 2008).*
Cen et al., "Small Molecular Compounds Inhibit HIV-1 Replication through Specifically Stabilizing APOBEC3G", 2010, Journal of Biological Chemistry, 285(22), pp. 16546-16552. (Year: 2010).*
Bennett et al., "A New Class of Antiretroviral Enabling Innate Immunity by Protecting APOBEC3 from HIV Vif-Dependent Degradation", 2018, Trends in Molecular Medicine, 24(5), pp. 507-520. (Year: 2018).*
National Center for Biotechnology Information. "PubChem Compound Summary for CID 148662725" PubChem, https://pubchem.ncbi.nlm.nih.gov/compound/148662725. Accessed Nov. 2, 2020; Create Aug. 12, 2020. (Year: 2020).*
Zhang et al., "Topotecan Inhibits Human Immunodeficiency Virus Type 1 Infection through a Topoisomerase-ndependent Mechanism in a Cell Line with Altered Topoisomerase I," Antimicrobial Agents and Chemotherapy 41 (5):977-981 (May 1997).
Yoshikawa et al., "Novel Camptothecin Analogues that Circumvent ABCG2-Associated Drug Resistance in Human Tumor Cells," International Journal of Cancer 110:921-927 (Mar. 24, 2004).
Bala et al., "Prodrug and Nanomedicine Approaches for the Delivery of the Camptothecin Analogue SN38," Journal of Controlled Release 172:48-61 (Aug. 6, 2013).
Zhang et al., "Identification of an HIV-1 Replication Inhibitor which Rescues Host Restriction Factor APOBEC3G in Vif-APOBEC3G Complex," Antiviral Research 122:20-27 (Aug. 1, 2015).
International Search Report issued in International Counterpart Application No. PCT/US2018/012098, dated Mar. 30, 2018.
Written Opinion issued in International Counterpart Application No. PCT/US2018/012098, dated Mar. 30, 2018.
Salter et al., "Structural Insights for HIV-1 Therapeutic Strategies Targeting Vif," Trends in Biochemical Sciences 39 (9):373-380 (Sep. 2014).
Hertzberg et al., "Modifications of the Hydroxy Lactone Ring of Camptothecin: Inhibitoin of Mammalian Topisomerase I and Biological Activity," J. Med. Chem. 32:715-720 (1989).
Jaxel et al., "Structure-Activity Study of the Actions of Camptothecin Derivatives on Mammalian Topoisomerase I Evidence for a Specific Receptor Site and a Relation to Antitumor Activity," Cancer Research 49:1465-1469 (Mar. 1989).
Redinbo et al., "Crystal Structure of Human Topoisomerase I in Covalent and Noncovalent Complexes with DNA," Science 279:1504-1513 (Mar. 1998).

(Continued)

*Primary Examiner* — My-Chau T. Tran
(74) *Attorney, Agent, or Firm* — FisherBroyles, LLP; Andrew K. Gonsalves, Esq.

(57) ABSTRACT

Disclosed herein are compounds useful for treating and/or preventing HIV infections and the transmission of HIV from an infected subject.

16 Claims, 3 Drawing Sheets

(56) References Cited

OTHER PUBLICATIONS

Xiao et al., "Effect of E-Ring Modifications in Camptothecin on Topoisomerase I Inhibition: A Quantum Mechanics Treatment," J. Org. Chern. 70:9584-9587 (Oct. 2005).

Pubmed Compound Summary for CID 60838, Irinotecan, U.S. National Library of Medicine, p. 1 (https://pubchem.ncbi.nlm.nih.gov/compound/irinotecan) (Jun. 24, 2005).

Zuo et al., "Small-Molecule Inhibition of Human Immunodeficiency Virus Type 1 Replication by Targeting the Interaction between Vif and ElonginC," J. Virology, 86(10):5497-5507 (2012).

Cutrell et al., "HIV Prevention Trial Design in an Era of Effective Pre-Exposure Prophylaxis," HIV Clinical Trials, 18 (5-6):177-188 (2017).

Nobeli et al., "Hydrogen Bonding Properties of Oxygen and Nitrogen Acceptors in Aromatic Heterocycles," J. Computational Chemistry, 18(16):2060-2074 (1997).

Danziger et al., "Automated Site-Directed Drug Design: A General Algorithm for Knowledge Acquisition about Hydrogen-Bonding Regions at Protein Surfaces," The Royal Society, Proceedings of the Royal Society of London. Series B, Biological Sciences, vol. 236, No. 1283, p. 101-113 (1989).

Li et al., "Camptothecin Inhibits Tat-Mediated Transactivation of Type 1 Human Immunodeficiency Virus," J. Biological Chemistry, 269(10):7051-7054 (1994).

Patani et al., "Bioisoterism: A Rational Approach in Drug Design," Chern. Rev., 96:3147-3176 (1996).

Zhang et al., "T-Cell Differentiation Factor CBF-β Regulates HIV-1 Vif-Mediated Evasion of Host Restriction," Nature, 181:376-380 (2012).

Bennett et al., "An Analog of Camptothecin Inactive Against Topoisomerase I Is Broadly Neutralizing of HIV-1 Through Inhibition of Vif-dependent APOBEC3G Degradation," Antiviral Research, 136:51-59 (Nov. 5, 2016).

* cited by examiner

COMPOUNDS, COMPOSITIONS, AND METHODS FOR TREATING HUMAN IMMUNODEFICIENCY VIRUS

CROSS REFERENCE TO RELATED APPLICATIONS

This application is a U.S. National Phase filing under 35 U.S.C. § 371 of International Application No. PCT/US2018/012098, filed Jan. 2, 2018, and published as WO 2018/128993-A1 on Jul. 12, 2018, which claims priority benefit of U.S. Provisional Patent Application Ser. No. 62/442,374, filed Jan. 4, 2017, the disclosures of which are hereby incorporated by reference herein in their entirety.

FIELD OF THE INVENTION

Disclosed herein are compounds useful for treating and/or preventing HIV infections and the transmission of HIV from an infected subject.

BRIEF DESCRIPTION OF THE FIGURES

FIG. 1A depicts the data points obtained for the compound having Formula I together with the logistic model regression curve [$EC_{50}$ 378 nM]. FIG. 1B depicts the data points obtained for the compound having Formula II together with the logistic model regression curve [$EC_{50}$ 362 nM]. FIG. 1C depicts the data points obtained for the compound having Formula III together with the logistic model regression curve [$EC_{50}$ 3869 nM].

FIG. 2A depicts the data points obtained for the compound having Figure I together with the logistic model regression curve [$EC_{50}$ 84 nM]. FIG. 2B depicts the data points obtained for the compound having Figure II together with the logistic model regression curve [$EC_{50}$ 99 nM]. FIG. 2C depicts the data points obtained for the compound having Figure III together with the logistic model regression curve [$EC_{50}$ 1200 nM].

DETAILED DESCRIPTION

Figure 1A:
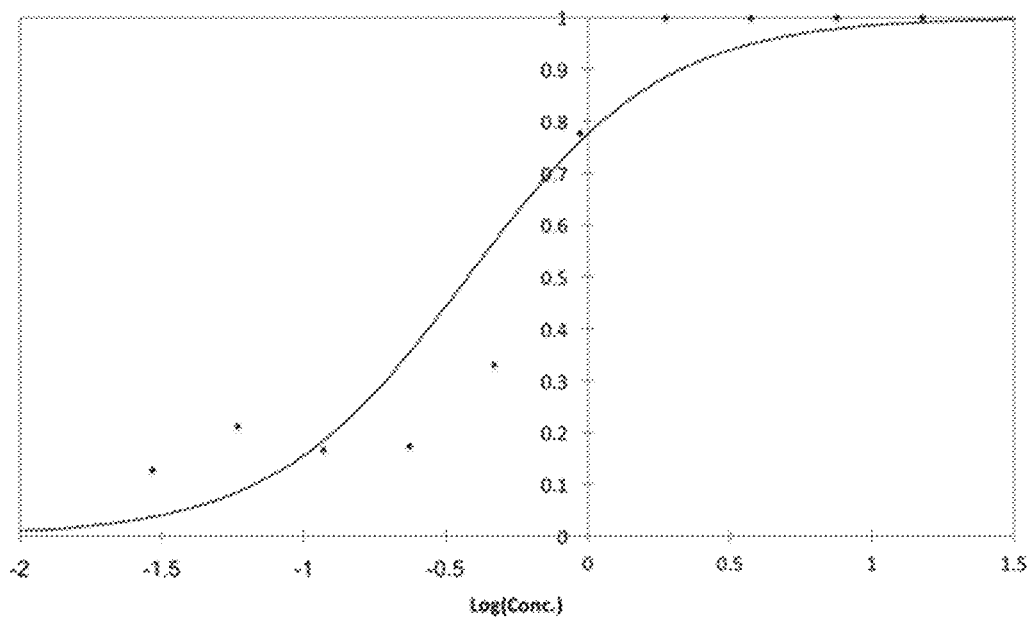
FIGS. 1A-1C are data points depicting the results of the Vif FqRET Multimerization Assay for the disclosed compounds. Circles (●) represent data points from the assay. The solid line represents the model dose response curve.

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Admixture" or "blend" is generally used herein means a physical combination of two or more different components "Excipient" is used herein to include any other compound that may be contained in or combined with one or more of the disclosed inhibitors that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

As used herein, the term "subject" refers to a human or an animal that has been diagnosed with Human Immunodeficiency Virus (HIV) or has tested positive for HIV. The term subject also includes humans or animals that have been exposed to HIV but are not symptomatic.

The term "treat" or other forms of the word such as "treated" or "treatment" is used herein to mean that administration of a compound, mixture of compounds or a composition of the present disclosure mitigates, cures, prevents or stops the transmission of HIV.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a chemotherapeutic agent" includes mixtures of two or more such chemotherapeutic agents, reference to "the compound" includes mixtures of two or more such compounds, for example, salts thereof, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Details associated with the embodiments described above and others are described below.

Disclosed herein are compounds that inhibit the self-association of Viral Infectivity Factor (Vif) in HIV-infected cells. Inhibition of Vif self-association prevents HIV from being transmitted from an infected cell. Vif binds to and induces the destruction of APOBEC3G (also referred to herein as "A3G"), which is a broad antiviral host-defense factor; in other words Vif destroys the body's own defense mechanism against HIV infection. Therefore, Vif is essential for HIV infection. Vif subunits interact to form multimers and this property has been shown to be necessary for HIV infectivity.

Without wishing to be limited by theory, the segment of Vif that mediates subunit interaction is the amino acid segment of Vif identified as proline-proline-leucine-proline (PPLP). As such, disclosed herein are methods for inhibiting Vif self-dimerization comprising administering either compounds or compositions, containing said compounds, that can disrupt Vif self-association (also referred to herein as "Vif dimerization" or "Vif multimerization").

Compounds

Disclosed herein are compounds which can disrupt Vif self-dimerization. The following is a listing of the disclosed compounds.

(S)-4,11-Diethyl-4,9-dihydroxy-1,2-dihydroquinolino[2',3':3,4]pyrrolo[1,2-b][2,7]naphthyridine-3,14(4H,12H)-dione having Formula I [also designated herein as "SN38-L"]:

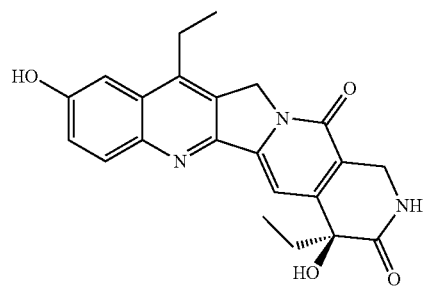

Formula I or pharmaceutically acceptable salts thereof. This compound is available from PharmaAgra Labs.

(S)-9-Amino-4,11-diethyl-4-hydroxy-1,2-dihydroquinolino[2',3':3,4]pyrrolo[1,2-b][2,7]naphthyridine-3,14(4H,12H)-dione having Formula II: [also designated herein as "O5-SN"]:

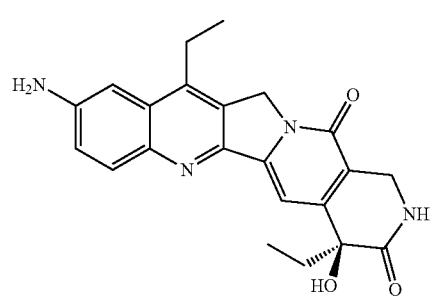

Formula II or pharmaceutically acceptable salts thereof. This compound is available from PharmaAgra Labs.

(S)-10-Amino-4-ethyl-4-hydroxy-1,2-dihydroquinolino[2',3':3,4]pyrrolo[1,2-b][2,7]naphthyridine-3,14(4H,12H)-dione having Formula III [also designated herein as "O5-9A"]:

Formula III

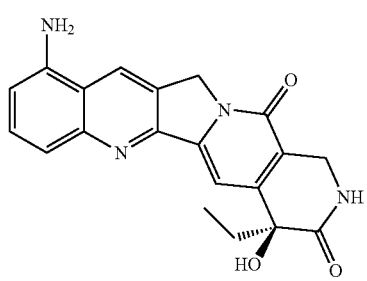

or pharmaceutically acceptable salts thereof. This compound is available from the National Cancer Institute's open repository under NSC #696881.

The present disclosure specifically disclaims 1,2-dihydroquinolino[2',3':3,4]pyrrolo[1,2-b][2,7]naphthyridine-3,14(4H,12H)-dione having the formula:

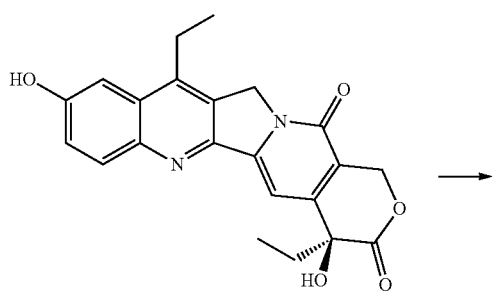

or all pharmaceutically acceptable salts thereof. As such, the disclosed compounds, methods, compositions, or prodrugs do not comprise this compound.

The disclosed compounds can be prepared by converting the corresponding camptothecin analogs from the lactone to the corresponding lactam. Scheme I below outlines the preparation of compound SN38-L having Formula I above as described in Example 1.

Scheme I

Reagents and conditions: (a) isopropyl amine; reflux, 2 hr.

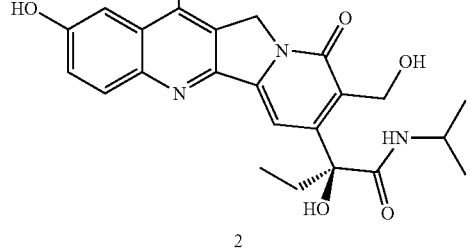

1

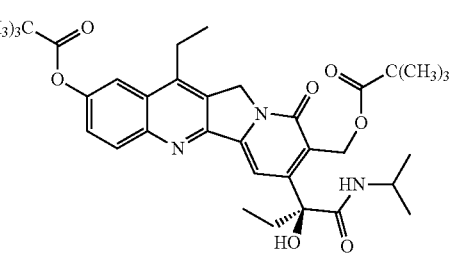

2

Reagents and conditions: (b) (CH$_3$)$_3$COCl, DMAP, TEA, CH$_2$Cl$_2$; -6° C. to rt, 18 hr.

2

3

Reagents and conditions: (c) NH$_3$, CH$_2$Cl$_2$; -33° C. to rt; 18 hr autoclave

3

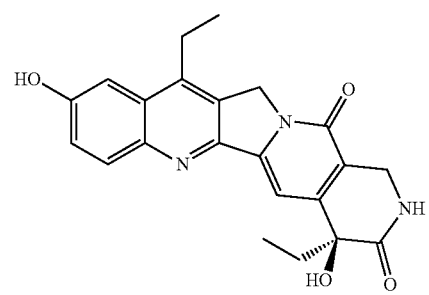

4 [SN38-L]

Example 1

(S)-4,11-Diethyl-4,9-dihydroxy-1,2-dihydroquinolino[2',3':3,4]pyrrolo[1,2-b][2,7]naphthyridine-3,14(4H,12H)-dione, SN38-L Preparation of (S)-2-(12-ethyl-2-hydroxy-8-(hydroxymethyl)-9-oxo-9,11-dihydroindolizino[1,2-b]quinolin-7-yl)-2-hydroxy-N-isopropylbutanamide, 2: 7-Ethyl-10-hydroxycamptothecin [CAS No. 86639-52-3 available from Carbosynth] was dissolved in isopropyl amine. The mixture was warmed to reflux. After 2 h, TLC (1:9 MeOH/DCM) showed the reaction was complete. The mixture was transferred to a 2 L RBF using chloroform (100 mL). The mixture was concentrated to dryness by rotary evaporation. The residue was dissolved in chloroform (700 mL) and concentrated to dryness on a rotary evaporator. The residue was dissolved in chloroform (700 mL) again, and concentrated to dryness on a rotary evaporator. The resulting solid was dried under high vacuum (<1.0 torr) for 18 hours affording 12.66 g (110%) yield of product 2 which was used without further purification.

Preparation of (S)-(12-ethyl-7-(2-hydroxy-1-(isopropylamino)-1-oxobutan-2-yl)-9-oxo-2-(pivaloyloxy)-9,11-dihydroindolizino[1,2-b]quinolin-8-yl)methyl pivalate, 3: Compound 2 and DMAP were suspended in dichloromethane (300 mL) and triethylamine. The heterogeneous mixture was cooled in a methanol/ice bath to an internal temperature of −6° C. Trimethyl acetyl chloride was dissolved in dichloromethane (60 mL) and the solution was added dropwise to the reaction mixture over 30 min keeping the temperature below 0° C. The reaction was allowed to warm to room temperature and stirred for 18 hours. TLC (1:9 MeOH/DCM) indicated the reaction was complete. The mixture was concentrated to dryness on a rotary evaporator. The residue was cooled in an ice bath and saturated NaHCO3 (200 mL) was added dropwise with stirring. The mixture was stirred for 90 minutes (convenience) and filtered. The filter cake was washed with water (200 mL) and heptane (200 mL). The solid was dried under high vacuum (<1 torr) for 18 hours to afford compound 3 (12.21 g, 83% yield) which was used without further purification.

Preparation of (S)-4,11-diethyl-4,9-dihydroxy-1,2-dihydroquinolino[2',3':3,4]-pyrrolo[1,2-b][2,7]naphthyridine-3,14(4H,12H)-dione, 4 [Formula I]: Compound 3 was suspended in dichloromethane (24 mL) in a stainless steel autoclave, liquid ammonia (200 mL) was added and the autoclave was sealed. The autoclave was allowed to warm to ambient temperature over 18 hours. The autoclave was then warmed to 60° C. for 90 min (225 psi) and then cooled in a −78° C. bath for an hour. The solution in the autoclave was transferred to a RBF and concentrated on a rotary evaporator. The solid was suspended in dichloromethane (3 mL) and sonicated for 10 minutes. The solid was collected by filtration, and triturated a second time with dichloromethane and sonication. The solid was suspended in 0.5 mol HCl (6 mL), sonicated 1 minute, and collected by filtration. The filter cake was washed with heptane (15 mL) and dried under high vacuum resulting in compound 4, SN38-L (1.82 g, 50.8% yield, and 96.8% purity by HPLC).

The synthesis of precursor 1 is disclosed in Sawada, S. et al., "Synthesis and antitumor Activity of 20(S)-Camptothecin Derivatives: Carbamate-Linked, Water-Soluble Derivatives of 7-Ethyl-10-hydroxycamptothecin," *Chem. Pharm. Bull.* 39(6) 1446-1454 (1991) which is included herein by reference.

The synthesis of the camptothecin precursors of O5-9A and O5-SN are disclosed in U.S. Pat. No. 4,473,692 issued Sep. 25, 1984 which is included herein by reference.

Prodrugs

Further disclosed herein are prodrugs of the disclosed compounds. The disclosed prodrugs are metabolically labile and upon administration are readily converted to the parent compound. Without wishing to be limited by theory, the disclosed prodrugs are metabolized by carboxylesterases in the blood, intestine and liver thereby providing the parent Vif self-dimerization inhibitor.

One non-limiting example of a disclosed prodrug is (S)-4,11-diethyl-4-hydroxy-3,14-dioxo-1,2,3,4,12,14-hexahydroquinolino[2',3':3,4]pyrrolo[1,2-b][2,7]naphthyridin-9-yl [1,4'-bipiperidine]-1'-carboxylate having Formula IV [also known herein as "Irino-L"]:

Formula IV

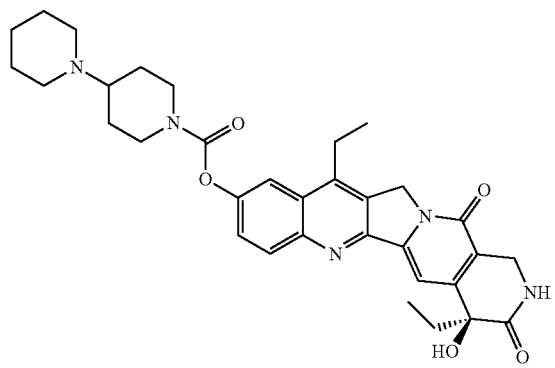 [SMILES: CCc1c2c(nc3ccc(OC(=O)N4CCC(N5CCCCC5)CC4)cc13)-c1cc3c(c(=O)n1C2)CNC(=O)[C@]3(O)CC]

or a pharmaceutically acceptable salt thereof. This compound is available from PharmaAgra Labs.

The disclosed pro-drug can be prepared according to Scheme II, or by a modification thereof known to the artisan, as described in Example 2 herein below.

Scheme II

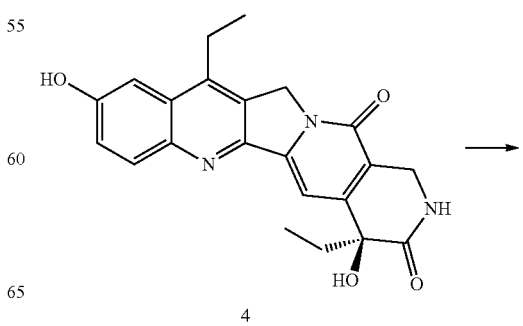

4

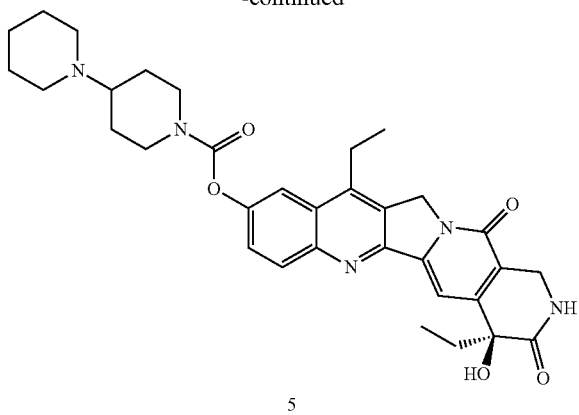

5

Reagents and conditions: (a) [1,4'-bipiperidine]-1'-carbonyl chloride, TEA, DMAP; -5° C. to rt.

Example 2

Preparation of (S)-4,11-diethyl-4-hydroxy-3,14-dioxo-1,2,3,4,12,14-hexahydro-quinolino[2',3':3,4]pyrrolo[1,2-b][2,7]naphthyridin-9-yl [1,4'-bipiperidine]-1'-carboxylate, 5: Compound 4 was suspended in CHCl₃ (100 mL), and triethylamine and DMAP were added. The flask was cooled in an ice bath to 1° C. [1,4'-bipiperidine]-1'-carbonyl chloride in CHCl₃ (50 mL) was added dropwise over 1 hour keeping the internal temperature below 5° C. The reaction mixture was allowed to warm to room temperature and stirred for 18 hours. Analysis of an aliquot of the reaction mixture by TLC indicated a trace of starting material, 4. The reaction mixture was heated to 35° C. for 2 hours, and then concentrated to dryness on a rotary evaporator. The residue was treated by dropwise addition of saturated NaHCO₃ (300 mL) and stirred for 1 hour. The resulting solid was collected by filtration and washed with heptane (2×100 mL). The crude solid (4.5 g) was triturated in dichloromethane (200 mL) and the remaining trace solids were removed by filtration. The filtrate was dry loaded onto celite (10 g) and placed on top of a 300 g silica gel column. The column was eluted with a stepwise gradient of 5% to 20% (CHCl₃:MeOH: NH₄OH, 80/18/2) in dichloromethane increasing 2.5% every 500 mL of eluent and collecting 100 mL fractions. The product eluted in fractions 14 to 48. None of the fractions were pure product. The fractions containing product were concentrated resulting in 2.5 g of solid. A 100 mg sample was used to form the HCl salt. The salt was crystallized from EtOH/MTBE. The resulting white solid turned to gum while collecting by filtration. The bulk was taken up in 1N HCl (30 mL) and washed with dichloromethane and MTBE. The mixture was basified with NH4OH (pH=9) and extracted with dichloromethane (3×75 mL). The combined organic layer was washed with brine and concentrated. The material was dry loaded onto celite and placed on top of a 100 g silica gel column. The column was eluted with a step wise gradient of 1.2% to 16.5% (95% MeOH and 5% NH4OH) in dichloromethane increasing 3% every 250 mL and collecting 20 mL fractions. Fractions 29-36 where combined to give compound 5 (850 mg, 13.5% yield, >96% purity by HPLC).

The general synthesis of other prodrugs suitable for use in the disclosed compositions and methods can be found in Sawada, S. et al., "Synthesis and antitumor Activity of 20(S)-Camptothecin Derivatives: Carbamate-Linked, Water-Soluble Derivatives of 7-Ethyl-10-hydroxycamptothecin," *Chem. Pharm. Bull.* 39(6) 1446-1454 (1991).

Compositions

Disclosed herein are composition effective for treating HIV. The compositions can comprise one or more compounds that inhibit Vif self-association, enhances APOBEC3G activity or causes RNA mutations that produce defective HIV virions.

In one aspect the compositions comprise:
a) one or more compounds that inhibit Vif self-association, enhances APOBEC3G activity or causes RNA mutations that produce defective HIV virions; and
b) a pharmaceutically acceptable carrier.

In one embodiment of this aspect the compositions comprise:
a) one or more or the disclosed compounds; and
b) a pharmaceutically acceptable carrier.

In one example of this embodiment of this aspect the compositions comprise:
a) SN38-L [(S)-4,11-diethyl-4,9-dihydroxy-1,2-dihydroquinolino[2',3':3,4]-pyrrolo[1,2-b][2,7]naphthyridine-3,14(4H,12H)-dione] or a pharmaceutically acceptable salt thereof; and
b) a pharmaceutically acceptable carrier.

In another example of this embodiment of this aspect the compositions comprise:
a) O5-SN [(S)-9-amino-4,11-diethyl-4-hydroxy-1,2-dihydroquinolino[2',3':3,4]-pyrrolo[1,2-b][2,7]naphthyridine-3,14(4H,12H)-dione] or a pharmaceutically acceptable salt thereof; and
b) a pharmaceutically acceptable carrier.

In a further example of this embodiment of this aspect the compositions comprise:
a) O5-9A [(S)-10-Amino-4-ethyl-4-hydroxy-1,2-dihydroquinolino[2',3':3,4]pyrrolo[1,2-b][2,7]naphthyridine-3,14(4H,12H)-dione] or a pharmaceutically acceptable salt thereof; and
b) a pharmaceutically acceptable carrier.

In another aspect the disclosed compositions comprise:
a) one or more compounds that inhibit Vif self-association, enhances APOBEC3G activity or causes RNA mutations that produce defective HIV virions;
b) one or more pharmaceutically acceptable ingredients; and
c) a pharmaceutically acceptable carrier.

Pharmaceutically Acceptable Ingredients

Pharmaceutically acceptable ingredients are ingredients that are compatible with the other ingredients in the formulation, i.e., active compounds, carriers and the like. Non-limiting examples of pharmaceutically acceptable ingredients includes buffers, stabilizers, excipients and the like.

Pharmaceutically Acceptable Salts

As used herein, "pharmaceutically acceptable salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Non-limiting examples of salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like Carriers The disclosed compositions can comprise a liquid carrier when not in the solid form. The user can add a liquid carrier to a dry or solid formulation to complete the composition, for example, the user in one embodiment will add an amount of water to a solid form of the compounds disclosed herein. In one embodiment, water is the carrier. In another embodiment, the carrier can be $C_1$-$C_{10}$ linear, branched, and cyclic aliphatic alcohols either alone or in combination with water.

Combination Therapy

Disclosed herein are compositions comprising one or more pharmaceutically active ingredients which have also found use in the treatment of subjects infected with HIV or those subjects susceptible to having HIV transmitted to them. Without wishing to be limited by theory, the following summaries provide are non-limiting examples of chemotherapeutic agents suitable for use in a combination therapy with the disclosed compounds, prodrugs and salts thereof because these agents attack HIV by an entirely different mechanism than the disclosed compounds.

Indinavir

HIV-1 protease is an enzyme required for the proteolytic cleavage of the viral polyprotein precursors into the individual functional proteins found in infectious HIV-1. This compound binds to the protease active site and inhibits the activity of the enzyme. As such, indinavir acts to regulate HIV by inhibiting the virus' critical protease activity.

Raltegravir Raltegravir in an integrase inhibitor. As such, raltegravir acts to regulate a key enzyme in the replication mechanism of HIV. The HIV integrase is responsible for the transfer of virally encoded DNA into the host chromosome which is a necessary event in retroviral replication.

Nevirapine

Nevirapine is a non-nucleoside reverse transcriptase inhibitor (NNRTI) of HIV-1 which blocks HIV-1 RNA-dependent and DNA-dependent DNA polymerase activities by causing a disruption of the enzyme's catalytic site. Nevirapine does this by binding directly to the reverse transcriptase (RT).

Azidothymidine (AZT)

AZT, a thymidine analogue, works by selectively inhibiting HIV's reverse transcriptase, the enzyme that the virus uses to make a DNA copy of its RNA. Thus AZT inhibits HIV replication without affecting the function of uninfected cells.

In one aspect of the disclosed combination therapies the compositions comprise:
 a) one or more compounds that inhibit Vif self-association, enhances APOBEC3G activity or causes RNA mutations that produce defective HIV virions; and
 b) one or more anti-HIV therapies which act in manner not related to the inhibition of Vif self-association.

In one embodiment of this aspect the compositions comprise:
 a) one or more or the disclosed compounds; and
 b) one or more anti-HIV therapies which act in manner not related to the inhibition of Vif self-association.

In one example of this embodiment of this aspect the compositions comprise:

a) SN38-L [(S)-4,11-diethyl-4,9-dihydroxy-1,2-dihydroquinolino[2',3':3,4]-pyrrolo[1,2-b][2,7]naphthyridine-3,14(4H,12H)-dione] or a pharmaceutically acceptable salt thereof; and
 b) an anti-HIV agent chosen from indinavir, raltegravir, nevirapine, azidothymidine, or mixtures thereof.

In another example of this embodiment of this aspect the compositions comprise:
 a) O5-SN [(S)-9-amino-4,11-diethyl-4-hydroxy-1,2-dihydroquinolino[2',3':3,4]-pyrrolo[1,2-b][2,7]naphthyridine-3,14(4H,12H)-dione] or a pharmaceutically acceptable salt thereof; and
 b) an anti-HIV agent chosen from indinavir, raltegravir, nevirapine, azidothymidine, or mixtures thereof.

In a further example of this embodiment of this aspect the compositions comprise:
 a) O5-9A [(S)-10-Amino-4-ethyl-4-hydroxy-1,2-dihydroquinolino[2',3':3,4]-pyrrolo[1,2-b][2,7]naphthyridine-3,14(4H,12H)-dione] or a pharmaceutically acceptable salt thereof; and
 b) an anti-HIV agent chosen from indinavir, raltegravir, nevirapine, azidothymidine, or mixtures thereof.

Disclosed herein is the combination therapy comprising SN38-L and indinavir. Disclosed herein is the combination therapy comprising SN38-L and raltegravir. Disclosed herein is the combination therapy comprising SN38-L and nevirapine. Disclosed herein is the combination therapy comprising SN38-L and AZT. Disclosed herein is the combination therapy comprising O5-SN and indinavir. Disclosed herein is the combination therapy comprising O5-SN and raltegravir. Disclosed herein is the combination therapy comprising O5-SN and nevirapine. Disclosed herein is the combination therapy comprising O5-SN and AZT. Disclosed herein is the combination therapy comprising O5-9A and indinavir. Disclosed herein is the combination therapy comprising O5-9A and raltegravir. Disclosed herein is the combination therapy comprising O5-9A and nevirapine. Disclosed herein is the combination therapy comprising O5-9A and AZT.

The above combinations include the pharmaceutically acceptable salts of the disclosed compounds or prodrugs thereof.

Table I shows the selectivity of the adjunct therapeutic agents biological activity versus 2 of the disclosed compounds. This table details the fact that the recited agents for use in combination therapies as disclosed herein are effective by different mechanisms than Vif inhibition and SN38-L and O5-SN are inactive against these other HIV targets (i.e. protease, integrase and reverse transcriptase).

TABLE I

| compound | protease assay, $IC_{50}$ | integrase assay, $IC_{50}$ | reverse transcriptase, $IC_{50}$ |
| --- | --- | --- | --- |
| SN38-L | >100 μM | >100 μM | >100 μM |
| O5-SN | >100 μM | >100 μM | >100 μM |
| indinavir | 30 Nm | >10 μM | >10 μM |
| raltegravir | ND | 69 nM | >10 μM |
| AZT | ND | ND | 20 nM |
| nevirapine | ND | ND | 230 nM |

For the assays listed in Table I, the integrase assay was conducted using the XpressBio HIV-1 Integrase Assay Kit according to the manufacture's protocol. The protease assay was conducted with the Anthranilyl (Abz)-HIV Protease Substrate (Bachem H-2992), a hexapeptide FRET substrate derived from the p24/p15 cleavage site of the viral gag-pol poly-protein, which allows the screening of potential HIV protease inhibitors. 1 mM Abz-Substrate was diluted with Assay Buffer to a working stock of 20 μM. A 50 μM stock HIV-1 protease (received from Sook-kyung Lee (UNC)) was diluted with Assay Buffer (50 mM HEPES, pH 6.8, 150 mM NaCl, and 1% DMSO) to a working stock of 100 nM. 2 μl 100 nM HIV-1 Protease along with 2 uL 20 μM Abz Substrate was added into each well and incubated at room temperature (avoiding light) for 1 hour before being read on an Envision plate reader (Perkin Elmer) excitation at 280 nm, emission at >435 nm. The reverse transcriptase assay utilized purified recombinant HIV (pNL4-3) heterodimeric (p66/p51) Reverse Transcriptase (RT) that was purchased from a commercially available source. The assay was performed in 96-well filter plate, where RT activity was determined by the incorporation of radiolabeled deoxyribonucleotides into the newly synthesized DNA strand. The RT reaction mixture contained in vitro transcribed viral RNA derived from the HIV-1$_{NL4-3}$ 5'-LTR region (position 454 to 652) and primer that is complementary to the primer binding site (PBS, nucleotide residues nucleotides 636 to 652), radiolabeled deoxyribonucleotide, dNTPs and reverse transcriptase. Briefly, the reaction was carried out in a volume of 50 μl containing 50 mM Tris HCl, pH 7.8, 50 mM KCl, 5 mM MgCl$_2$, 1 mM DTT, 50 μM each of dATP, dCTP, dGTP, 50 nM dTTP, 1 μCi of [$^3$H] dTTP (70-90 Ci/mM) and 5 nM template/primer. The reaction was initiated by the addition of 10 nM RT. For compound screening, serially diluted test articles were added to the reaction followed by the addition of RT. The reaction mixture was incubated at 37° C. for 1 h, and then quenched by the addition of ice-cold trichloroacetic acid (TCA) to the final concentration of 10%. The plate was incubated at 4° C. for 1 h to precipitate the synthesized DNA, then rinsed 3-times with 10% TCA and 1 time with 70% ethanol. After addition of 25 μl scintillation fluid to completely dried wells, radioactivity is counted by Micro-Beta scintillation counter. The reduction of radioactivity represents the potency of compound inhibition.

Methods

Without wishing to be limited by theory, APOBEC3G integrates with viral particles and inhibits viral replication when Vif is disabled. In the absence of a functional Vif, APOBEC3G is incorporated into viral particles and is bound to the viral RNA upon release of the viral proteins into the target cell. During reverse transcription of the viral RNA into proviral DNA APOBEC3G causes dC to dU hypermutations on the viral minus strand that is single-stranded in the small window of time before the positive strand can be synthesized. These mutated proviral DNA strands are then either degraded by DNA repair machinery recognizing dU in DNA or they are incorporated into the host genome with dG to dA mutations in the positive strand. This results in the reverse transcriptase reading a dU mutation as needing a dA complementary nucleotide instead of the actual dG. The virus uses the host cell's machinery to produce mutated viral RNA and proteins; these mutations cause RNA missense and, therefore, stop codons that are catastrophic for viral function. The result is the production of progeny virions that are defective and, thereby, non-infective. Therefore, enhancement of APOBEC3G in the cell leads to non-infectivity. Disclosed herein are methods of enhancing APOBEC3G activity in a cell by inhibiting Vif mediated APOBEC3G destruction.

Disclosed herein are methods for treating HIV infection. Further disclosed are methods for preventing the replication of HIV in vitro, in vivo and ex vivo. Still further disclosed are methods for preventing the transmission of HIV from a subject that is infected with HIV to a subject that is not infected or does not test positively for an HIV infection.

Disclosed herein is a method for treating a subject having an HIV infection, comprising contacting the subject with an effective amount of a compound that prevents Vif mediated inhibition of APOBEC3G antiviral activity.

In one embodiment the compound is chosen from SN38-L, O5-SN, 05-9A, or mixtures thereof.

In one example of this embodiment the compound is SN38-L [(S)-4,11-Diethyl-4,9-dihydroxy-1,2-dihydroquinolino[2',3':3,4]pyrrolo[1,2-b][2,7]naphthyridine-3,14(4H, 12H)-dione] or a pharmaceutically acceptable salt thereof.

In another example of this embodiment the compound is O5-SN [(S)-9-Amino-4,11-diethyl-4-hydroxy-1,2-dihydroquinolino[2',3':3,4]pyrrolo[1,2-b][2,7]naphthyridine-3,14 (4H,12H)-dione] or a pharmaceutically acceptable salt thereof.

In a further example of this embodiment the compound is O5-9A [(S)-10-Amino-4-ethyl-4-hydroxy-1,2-dihydroquinolino[2',3':3,4]pyrrolo[1,2-b][2,7]naphthyridine-3,14(4H, 12H)-dione] or a pharmaceutically acceptable salt thereof.

Further disclosed herein is a method for treating a subject having an HIV infection, comprising contacting the subject with an effective amount of a compound that prevents the destruction of APOBEC3G.

In one embodiment the compound is chosen from SN38-L, O5-SN, 05-9A, or mixtures thereof.

In one example of this embodiment the compound is SN38-L [(S)-4,11-Diethyl-4,9-dihydroxy-1,2-dihydroquinolino[2',3':3,4]pyrrolo[1,2-b][2,7]naphthyridine-3,14(4H, 12H)-dione] or a pharmaceutically acceptable salt thereof.

In another example of this embodiment the compound is O5-SN [(S)-9-Amino-4,11-diethyl-4-hydroxy-1,2-dihydroquinolino[2',3':3,4]pyrrolo[1,2-b][2,7]naphthyridine-3,14 (4H,12H)-dione] or a pharmaceutically acceptable salt thereof.

In a further example of this embodiment the compound is O5-9A [(S)-10-Amino-4-ethyl-4-hydroxy-1,2-dihydroquinolino[2',3':3,4]pyrrolo[1,2-b][2,7]naphthyridine-3,14(4H, 12H)-dione] or a pharmaceutically acceptable salt thereof.

Also disclosed herein is a method for treating a subject having an HIV infection, comprising contacting the subject with an effective amount of a compound that prevents the destruction of APOBEC3G by preventing the self-association of the HIV Vif protein.

In one embodiment the compound is chosen from SN38-L, O5-SN, 05-9A, or mixtures thereof.

In one example of this embodiment the compound is SN38-L [(S)-4,11-Diethyl-4,9-dihydroxy-1,2-dihydroquinolino[2',3':3,4]pyrrolo[1,2-b][2,7]naphthyridine-3,14(4H, 12H)-dione] or a pharmaceutically acceptable salt thereof.

In another example of this embodiment the compound is O5-SN [(S)-9-Amino-4,11-diethyl-4-hydroxy-1,2-dihydroquinolino[2',3':3,4]pyrrolo[1,2-b][2,7]naphthyridine-3,14 (4H,12H)-dione] or a pharmaceutically acceptable salt thereof.

In a further example of this embodiment the compound is O5-9A [(S)-10-Amino-4-ethyl-4-hydroxy-1,2-dihydroquinolino[2',3':3,4]pyrrolo[1,2-b][2,7]naphthyridine-3,14(4H, 12H)-dione] or a pharmaceutically acceptable salt thereof.

Still further disclosed herein is a method for treating a subject having an HIV infection, comprising contacting the subject with an effective amount of a compound that prevents proline-proline-leucine-proline mediated subunit interaction between two Vif proteins. In one embodiment the compound is chosen from SN38-L, O5-SN, O5-9A, or mixtures thereof.

Disclosed herein is the use of a compound for preparing a medicament for treating a subject having an HIV infection, wherein the compound prevents Vif self-association.

Further disclosed herein is the use of a compound for preparing a medicament for treating a subject having an HIV infection, wherein the compound prevents the destruction of APOBEC3G and APOBEC3F.

Also disclosed herein is the use of a compound for preparing a medicament for treating a subject having an HIV infection, wherein the compound prevents proline-proline-leucine-proline mediated subunit interaction between two Vif proteins.

Still further disclosed herein is the use of a compound for preparing a medicament for treating a subject having an HIV infection, wherein the compound prevents formation of Vif multimers.

Formulations

The disclosed pharmaceutical compositions can be prepared, packaged, or sold in the form of a sterile injectable aqueous or oily suspension or solution. The suspension or solution can be formulated according to the known art, and can comprise, in addition to the disclosed compounds, additional ingredients such as the dispersing agents, wetting agents, or suspending agents described herein. Such sterile injectable formulations can be prepared using a non-toxic peritoneal-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The term "pharmaceutical composition" is used interchangeably with the term "medicament." For example, as used herein above the use of the disclosed compounds or any compound that can prevent formation of Vif multimers, prevents proline-proline-leucine-proline mediated subunit interaction between two Vif proteins, or prevents the destruction of APOBEC3G and APOBEC3F.

The disclosed pharmaceutical compositions that are useful in the disclosed methods can be administered, prepared, packaged, and/or sold in formulations suitable for oral, rectal, vaginal, peritoneal, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The disclosed compositions can be administered via numerous routes, including, but not limited to, oral, rectal, vaginal, peritoneal, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

As used herein, "peritoneal administration" of a pharmaceutical composition includes any route of administration characterized by physical breaching of a tissue of a subject and administration of the pharmaceutical composition through the breach in the tissue. Peritoneal administration thus includes, but is not limited to, administration of a pharmaceutical composition by injection of the composition, by application of the composition through a surgical incision, by application of the composition through a tissue-penetrating non-surgical wound, and the like. In particular, peritoneal administration is contemplated to include, but is not limited to, subcutaneous, intraperitoneal, intramuscular, intrasternal injection, and kidney dialytic infusion techniques.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Procedures

Disclosed herein are procedures that can screen for Vif multimerization and Vif-dependent APOBEC3G degradation along with target identification screens and counter screens against alternative HIV targets. Also disclosed herein are procedures for testing antiviral activity against multiple isolates representing all clades of HIV along with drug resistant HIV isolates.

The disclosed compounds O5-9A, SN38-L and O5-SN all block Vif multimerization and Vif-dependent A3G degradation, but do not inhibit topoisomerase I (TOP1) as do other anti-HIV compounds, for example, camptothecin. The disclosed compounds block HIV infection in PBMCs with nanomolar efficacy with low toxicity up to the micromolar range. Moreover, these compounds have selective activity, they possess no activity against other viral proteins of HIV, i.e., proteases, integrases and reverse transcriptases.

FgRET Assay for Vif Multimerization Inhibition:

The quenched fluorescence resonance energy transfer (FgRET) cell-based assay utilized expression of pNL4-3 Vif (accession no. M19921) tagged separately with either a EGFP fluorophore (EGFP-V5-Vif) or a REACh2 quencher (Vif-HA-REACh2) in the pIRES-P vector. The Vif multimerization assay was established through robotic co-transfection of HEK293T (293T) cells with Turbofect (Thermo) and optimized for input plasmid ratio (1:4, fluorophore to quencher) to achieve maximum quench of fluorescent signal. EGFP fluorescence was quantified 24 hours after transfection with a BioTek Synergy4 plate reader (ex=485 nm, em=528 nm) followed by the addition of 0-30 µM compound. The plates were read a second time 24 hours after compound addition. The differential between the first and second read in each well was quantified relative to the DMSO control to determine the change in relative fluorescence units (ΔRFU)

The interaction of 2 molecules of Vif (i.e. dimerization) enables quenching of Enhanced Green Fluorescent Protein (EGFP) signal by Resonance Energy Accepting Chromophore 2 (REACh2), a dark mutant of yellow fluorescent protein that is capable of accepting the EGFP donor fluorescence and quenching its signal without an acceptor signal.

Figure 1B:
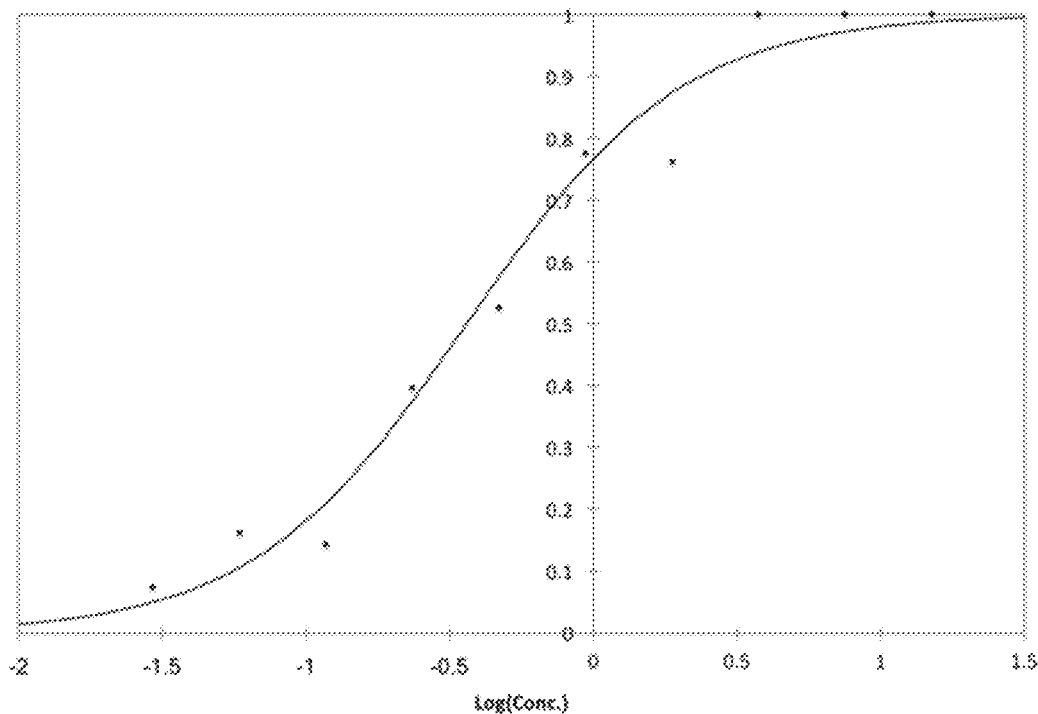
Figure 1C:
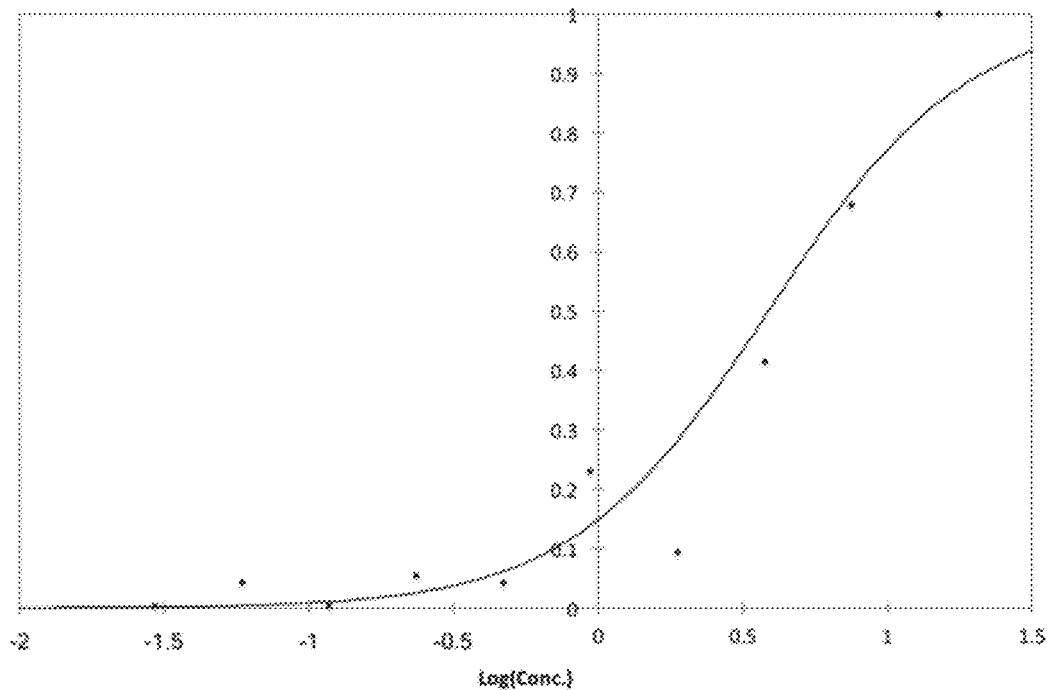

FIG. 1A depicts the data points obtained for the compound SN38-L having Figure I together with the logistic model regression curve [$EC_{50}$ 378 nM]. FIG. 1B depicts the data points obtained for the compound O5-SN having Formula II together with the logistic model regression curve [$EC_{50}$ 362 nM]. FIG. 1C depicts the data points obtained for the compound O5-9A having Formula III together with the logistic model regression curve [$EC_{50}$ 3869 nM]. Circles (●) represent data points from the assay. As seen in FIGS. 1A-1C, each of these molecules have strong activity in the Vif FqRET Multimerization Assay.

Vif-Dependent APOBEC3G Degradation Assay:

APOBEC3G-V5-mCherry was stably expressed from the pIRES-P vector in 293T cells under puromycin selection. Fifty ng of plasmid expressing Vif-HA (accession no. AB573087) was transfected into the cells in 384-well format with Turbofect on a liquid handling robot. Four hours after transfection the compounds were added to cells in a range from 0-15 µM. Twenty-four hours after compound addition mCherry fluorescence was read on a BioTek Synergy4 plate reader (ex=587 nm, em=610 nm). Relative fluorescence units (RFU) from compound treated wells were quantified using thresholds set by the −Vif (positive control) and +Vif (negative control).

Figure 2A:
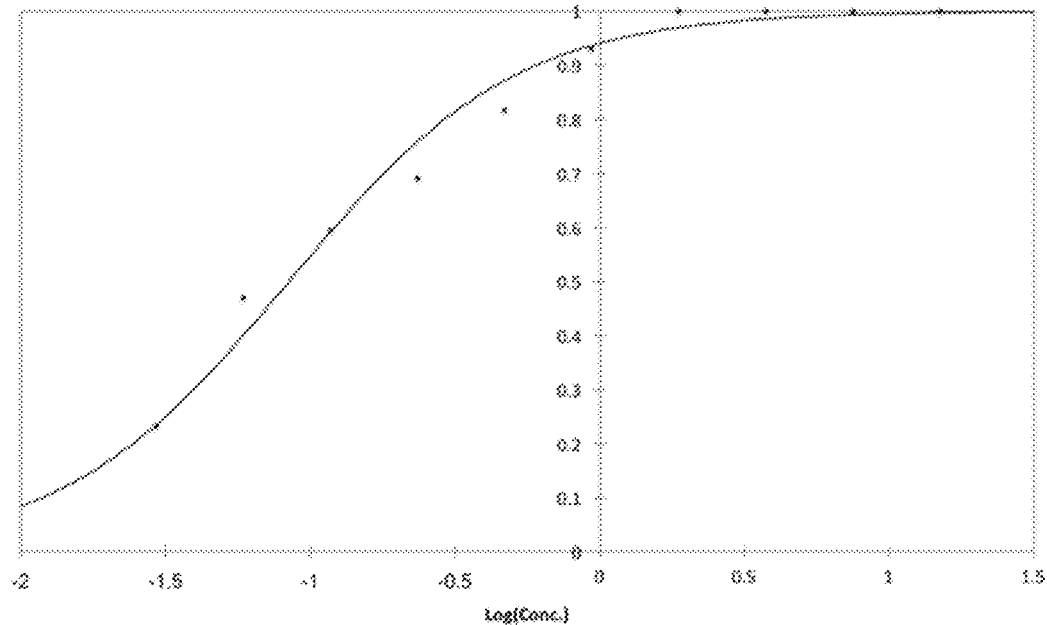
FIGS. 2A-2C are data points depicting the results of the A3G Degradation Assay for the disclosed compounds. Circles (●) represent data points from the assay. The solid line represents the model dose response curve.
Figure 2B:
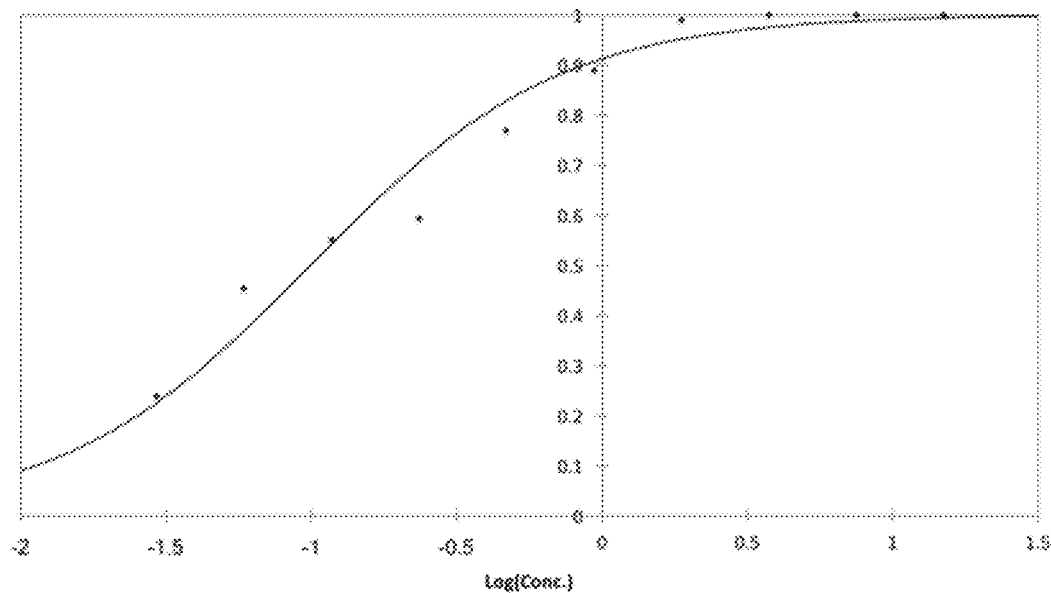
Figure 2C:
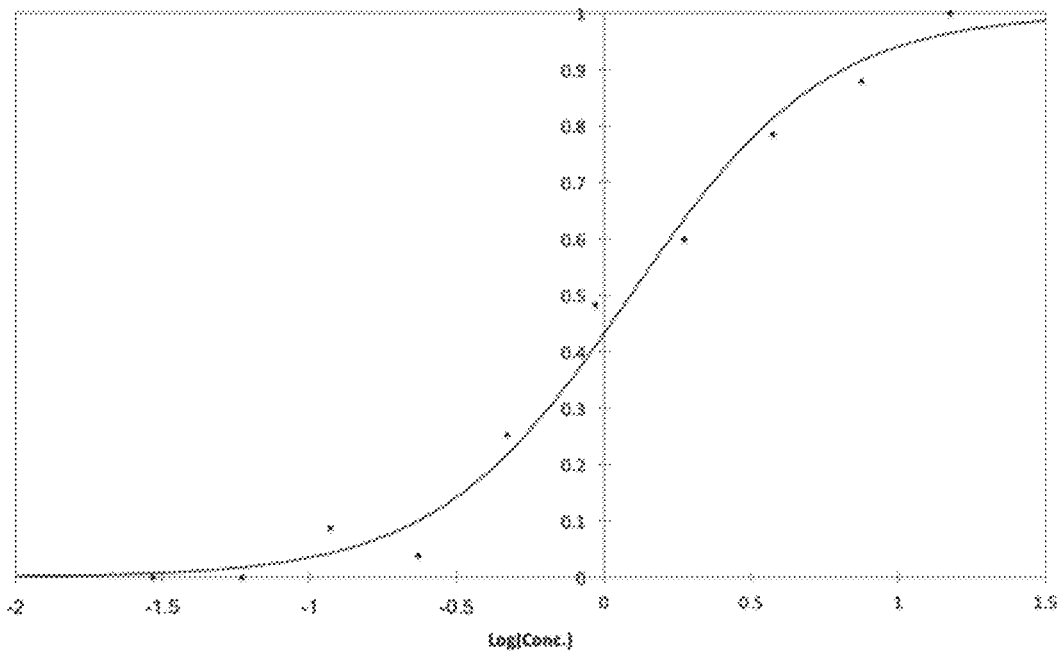

FIG. 2A depicts the data points obtained for SN38-L the compound having Formula I together with the logistic model regression curve [$EC_{50}$ 84 nM]. FIG. 2B depicts the data points obtained for O5-SN the compound having Formula II together with the logistic model regression curve [$EC_{50}$ 99 nM]. FIG. 2C depicts the data points obtained for O5-9A the compound having Formula III together with the logistic model regression curve [$EC_{50}$ 1200 nM]. Circles (●) represent data points from the assay. As seen in FIGS. 1A-1C, each of these molecules have strong activity in the Vif-dependent APOBEC3G Degradation Assay.

PBMC Acute Infection:

PHA-stimulated cells from at least two normal donors were pooled (i.e. mixed together), diluted in fresh medium to a final concentration of $1 \times 10^6$ cells/mL, and plated in the interior wells of a 96-well round bottom microplate at 50 µL/well ($5 \times 10^4$ cells/well). Pooling of mononuclear cells from more than one donor was used to minimize the variability observed between individual donors in quantitative and qualitative differences in HIV infection and overall response to the PHA and IL-2 of primary lymphocyte populations. Each plate contained virus control wells (cells plus virus) and experimental wells (drug plus cells plus virus) of either 00KE_KER2008 (Subtype A), IIIB (Subtype B), or 98US_MSC5016 (Subtype C). Test drug dilutions were prepared at a 2× concentration and 100 µL of each concentration was placed in appropriate wells. Fifty µL of a predetermined dilution of virus stock was placed in each test well (final MOI≅0.1). After this period, cell-free supernatant samples were collected for analysis of reverse transcriptase (RT) activity with an RT assay. Table II below shows the results of this Assay for the disclosed compounds. In the Table below $SI_{50}=CC_{50}/EC_{50}$ and $SI_{90}=CC_{90}/EC_{90}$.

TABLE II

| HIV Isolate | Subtype | $EC_{50}$ (µM) | $CC_{50}$ (µM) | $SI_{50}$ | $EC_{90}$ (µM) | $CC_{90}$ (µM) | $SI_{90}$ |
|---|---|---|---|---|---|---|---|
| Compound O5-9A having A3G degradation at 1.0 µM ||||||||
| 00KE-KER2008 | A | 0.05 | 9.32 | 185 | 0.23 | >100 | >435 |
| IIIB | B | 0.15 | 10.0 | 68 | 0.31 | >100 | >318 |
| 98US_MSC5016 | C | 0.06 | 9.32 | 154 | 0.22 | >100 | >455 |
| Compound O5-SN having A3G degradation at 0.084 µM ||||||||
| 00KE-KER2008 | A | 0006 | 2.53 | 422 | 0.018 | >100 | >5618 |
| IIIB | B | 0.008 | 6.29 | 753 | 0.025 | >100 | >4020 |
| 98US_MSC5016 | C | 0.006 | 2.53 | 457 | 0.020 | >100 | >5000 |
| Compound SN-38L having A3G degradation at 0.099 µM ||||||||
| 00KE-KER2008 | A | 0.004 | 1.18 | 315 | 0.015 | 27.9 | 1824 |
| IIIB | B | 0.010 | 5.79 | 464 | 0.028 | 27.9 | 982 |
| 98US_MSC5016 | C | 0.004 | 1.18 | 315 | 0.016 | 27.9 | 1766 |
| Prodrug Compound Irino-L having A3G degradation at 5.0 µM ||||||||
| 00KE-KER2008 | A | 2.26 | 17.7 | 8 | 7.71 | 82.8 | 11 |
| IIIB | B | 2.29 | 17.7 | 8 | 7.92 | 82.8 | 10 |
| 98US_MSC5016 | C | 1.85 | 17.7 | 10 | 7.11 | 82.8 | 12 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A composition for treating HIV, comprising:
   a) one or more compound that inhibits Vif self-association, enhances APOBEC3G activity or causes RNA mutations that produce defective HIV virions, wherein said one or more compound is chosen from:
      i) [(S)-4,11-diethyl-4,9-dihydroxy-1,2-dihydroquinolino[2',3':3,4]-pyrrolo[1,2-b][2,7]naphthyridine-3,14 (4H,12H)-dione having Formula I:

Formula I

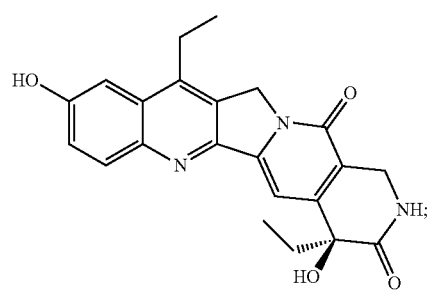

ii) (S)-9-Amino-4,11-diethyl-4-hydroxy-1,2-dihydroquinolino[2',3':3,4]pyrrolo[1,2-b][2,7]naphthyridine-3,14(4H,12H)-dione having Formula II:

Formula II

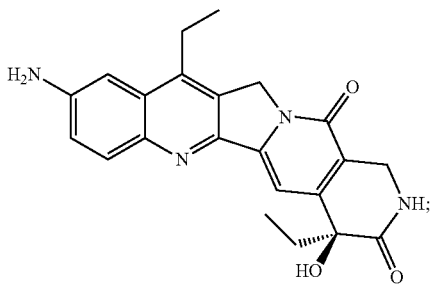

or iii) (S)-10-Amino-4-ethyl-4-hydroxy-1,2-dihydroquinolino[2',3':3,4]pyrrolo[1,2-b][2,7]naphthyridine-3,14(4H,12H)-dione having Formula III:

Formula III

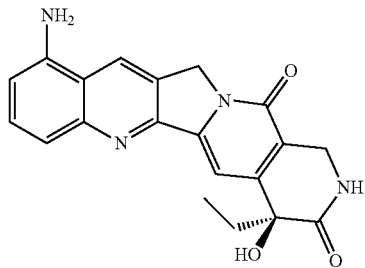

or pharmaceutically acceptable salts thereof; and b) a pharmaceutically acceptable carrier.

2. The composition according to claim 1, wherein the compound is [(S)-4,11-diethyl-4,9-dihydroxy-1,2-dihydroquinolino[2',3':3,4]-pyrrolo[1,2-b][2,7]naphthyridine-3,14(4H,12H)-dione.

3. The composition according to claim 1, wherein the compound is (S)-9-Amino-4,11-diethyl-4-hydroxy-1,2-dihydroquinolino[2',3':3,4]pyrrolo[1,2-b][2,7]naphthyridine-3,14(4H,12H)-dione.

4. The composition according to claim 1, wherein the compound is (S)-10-Amino-4-ethyl-4-hydroxy-1,2-dihydroquinolino[2',3':3,4]pyrrolo[1,2-b][2,7]naphthyridine-3,14(4H,12H)-dione.

5. The composition according to claim 1, further comprising a pharmaceutically acceptable ingredient.

6. The composition according to claim 5, wherein the pharmaceutically acceptable ingredient is a stabilizer.

7. The composition according to claim 5, wherein the pharmaceutically acceptable ingredient is a buffer.

8. The composition according to claim 1, wherein the carrier is water.

9. The composition according to claim 1 further comprising:
   one or more anti-HIV therapy that does not inhibit Vif self-association.

10. The composition according to claim 9, wherein the anti-HIV therapy that does not inhibit Vif self-association is chosen from indinavir, raltegravir, nevirapine, azidothymidine, camptothecin or mixtures thereof.

11. The composition according to claim 9, wherein said composition comprises:

a) a therapeutic system containing:
   i) from about 1% to about 99% by weight of said one or more compound that inhibits Vif self-association, enhances APOBEC3G activity or causes RNA mutations that produce defective HIV virions; and
   ii) from about 1% to about 99% by weight of said one or more anti-HIV therapy that does not inhibit Vif self-association; and b) a carrier.

12. A composition comprising a prodrug that inhibits Vif self-association, enhances APOBEC3G activity or causes RNA mutations that produce defective HIV virions, wherein said prodrug is (S)-4,11-diethyl-4-hydroxy-3,14-dioxo-1,2,3,4,12,14-hexahydroquinolino[2',3':3,4]pyrrolo[1,2-b][2,7]naphthyridin-9-yl [1,4'-bipiperidine]-1'-carboxylate having the formula:

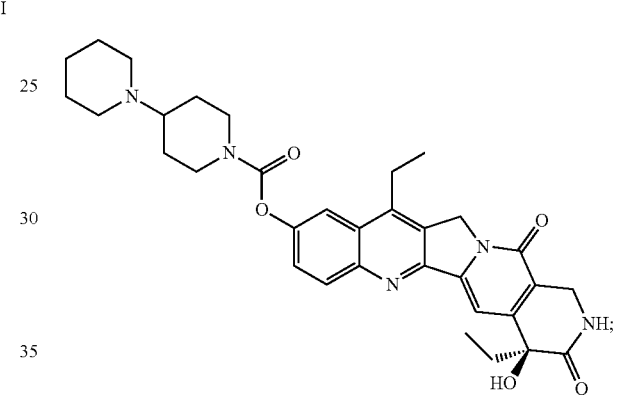

or a pharmaceutically acceptable salt thereof.

13. A method for treating a subject having an HIV infection, comprising contacting the subject with an effective amount of a compound that prevents Vif self-association, wherein said compound is chosen from:

i) [(S)-4,11-diethyl-4,9-dihydroxy-1,2-dihydroquinolino[2',3':3,4]-pyrrolo[1,2-b][2,7]naphthyridine-3,14(4H,12H)-dione having Formula I:

Formula I

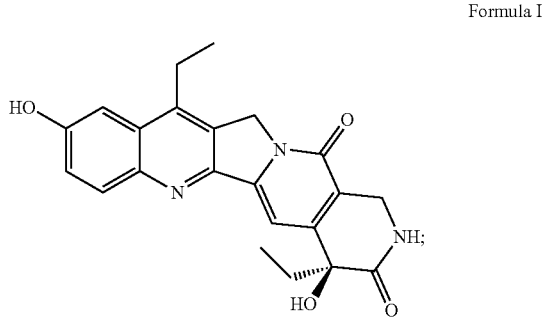 [SMILES: CCc1c2c(nc3ccc(O)cc13)-c1cc3c(c(=O)n1C2)CNC(=O)[C@]3(O)CC]

ii) (S)-9-Amino-4,11-diethyl-4-hydroxy-1,2-dihydroquinolino[2',3':3,4]pyrrolo[1,2-b][2,7]naphthyridine-3,14(4H,12H)-dione having Formula II:

Formula II

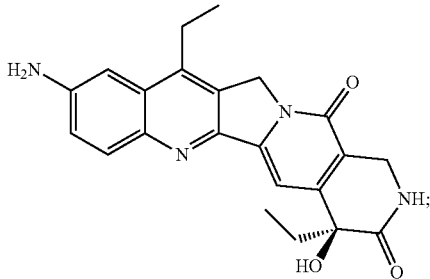

or iii) (S)-10-Amino-4-ethyl-4-hydroxy-1,2-dihydroquinolino[2',3':3,4]pyrrolo[1,2-b][2,7]naphthyridine-3,14(4H,12H)-dione having Formula III:

Formula III

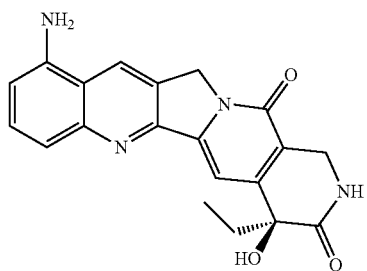

or pharmaceutically acceptable salts thereof.

14. The method according to claim 13, wherein the compound is (S)-4,11-diethyl-4,9-dihydroxy-1,2-dihydroquinolino[2',3':3,4]-pyrrolo[1,2-b][2,7]naphthyridine-3,14(4H,12H)-dione having Formula I:

Formula I

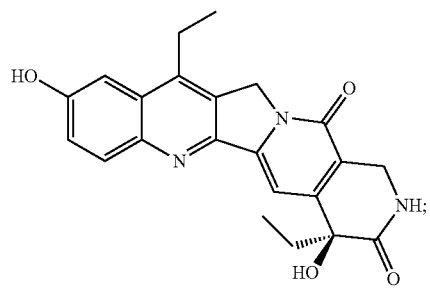

or pharmaceutically acceptable salts thereof.

15. The method according to claim 13, wherein the compound is selected from the group consisting of:

(a) (S)-9-Amino-4,11-diethyl-4-hydroxy-1,2-dihydroquinolino[2',3':3,4]pyrrolo[1,2-b][2,7]naphthyridine-3,14(4H,12H)-dione, and (b) (S)-10-Amino-4-ethyl-4-hydroxy-1,2-dihydroquinolino[2',3':3,4]pyrrolo[1,2-b][2,7]naphthyridine-3,14(4H,12H)-dione.

16. The method according to claim 13, further comprising administering a second anti-HIV therapy, wherein the second therapy does not inhibit Vif self-association, wherein said second therapy is a compound chosen from indinavir, raltegravir, nevirapine, azidothymidine, or camptothecin.

* * * * *